United States Patent [19]

Durante et al.

[11] Patent Number: 5,073,664
[45] Date of Patent: Dec. 17, 1991

[54] DIMERIZATION OF ALKANES WITH BARIUM PEROXIDE

[75] Inventors: Vincent A. Durante, West Chester; James E. Lyons, Wallingford, both of Pa.

[73] Assignee: Sun Refining and Marketing Company, Philadelphia, Pa.

[21] Appl. No.: 667,733

[22] Filed: Mar. 11, 1991

[51] Int. Cl.$^5$ .............................................. C07C 2/00
[52] U.S. Cl. .................. 585/700; 585/502; 585/510; 585/516; 585/520; 585/654; 585/656
[58] Field of Search ............... 585/500, 502, 510, 516, 585/520, 654, 656, 700

[56] References Cited

U.S. PATENT DOCUMENTS 2,422,692  6/1947  Mattox ................................ 585/700
4,205,194  5/1980  Mitchell, III et al. ............. 585/407

Primary Examiner—Curtis R. Davis
Assistant Examiner—E. D. Irzinski
Attorney, Agent, or Firm—Q. Todd Dickinson; Donald R. Johnson

[57] ABSTRACT

Propane is dimerized to 2,3-dimethylbutane with barium peroxide oxidizer.

5 Claims, No Drawings

DIMERIZATION OF ALKANES WITH BARIUM PEROXIDE

BACKGROUND OF INVENTION

Light alkanes are becoming increasingly abundant and lower in value as volatility restrictions limit their use in gasoline. At the same time aromatic hydrocarbons, which are the traditional sources of octane, are under fire from the Clean Air Act. A highly-branched paraffinic alkylate would be a very desirable high-octane alternative to aromatics. Such an alkylate is conventionally made from light olefins and isoparaffins, but the light olefins are very expensive relative to light alkanes. Thus, a process which could couple the light alkanes to give a highly-branched paraffinic product would be an economically attractive solution to both the problems of light alkane oversupply and high octane needs. No such process currently exists. Our invention provides one.

PRIOR ART

The oxidative coupling of methane to give ethane and ethylene has been widely studied over the past two decades. Catalysts for this process are reducible metal oxides such as PbO, MnO, LiO/MgO and many others. They are used with or without promoters. Temperatures required for the process exceed 650° C. which is well above the temperature of 450° C. at which the isoparaffin dimers of propane and butane crack.

In *Journal of Catalysis* (1990) pp. 121–122, Otsuka et al indicated that propane coupling could occur at low yield in a stoichiometric anaerobic reaction over sodium peroxide at 375° C. It is, however, difficult to regenerate the reduced sodium product with molecular oxygen.

SUMMARY OF INVENTION

Our invention is a process for the coupling or dimerization of propane and butane to form branched chain paraffins such as 2,3-dimethylbutane, methylpentane, etc., with a barium peroxide ($BaO_2$) regenerable oxidizer.

DETAILED DESCRIPTION OF INVENTION

Our invention is a process for the oxidative coupling, i.e., dimerization, of propane or butanes to branched alkanes. The oxidizer is barium peroxide. The reaction temperature is 200°–450° C., preferably 250°–400° C., more preferably 300°–400° C., and the reaction can be done in liquid or vapor phase at pressures of 100 to 2000 psig. preferably 400–1200 psig. The temperature will vary depending on both the processing arrangement employed and the feedstock, but the minimum temperature necessary is easily determined.

Barium peroxide is an article of commerce and readily available. It can be made by the direct combustion of barium or barium oxide in air or oxygen at 500°–600° C. Because of this, the lower oxides of barium formed from the $BaO_2$ in the oxidative dimerization of our invention are readily regenerable to $BaO_2$.

EXAMPLES

Commercially obtained barium peroxide powder (4 g.) was mixed with silica gel (0.7 g) as a diluent and packed into a stainless steel tubular reactor fitted with thermowell. A helium stream at 200 ml (NTP)/min. was passed through the bed at 375° C. for 2 hrs. to decompose superoxide contaminants. The temperature was then raised to 400° C., the helium flow rate was increased to 400 ml (NTP)/min and the pressure was increased to 800 psig. A single pulse of propane was then injected by an automated sampling valve into the helium stream. A mild exotherm was noted as the propane pulse passed through the barium peroxide bed.

The eluting desorption pulse was continuously sampled by a high pressure thermal conductivity detector and by an on-line mass spectrometer coupled through an open-split interface. A "slice" of the desorption pulse was also taken by a downstream sampling valve and independently analyzed by on-line gas chromatography. After this analysis of the eluted peak, the temperature of the bed was raised to above 575° C. while monitoring with the mass spectrometer to detect any additional desorbed products. Only oxygen was detected in this step in any run. After reoxidation with flowing air at 575° C., the propane pulse experiment was repeated several times at temperatures between 300° and 450° C.

At 400° C., both mass spec and GC analysis confirmed the production of 2,3-dimethylbutane (2,3-DMB) and 2-methylpentane (2-MP) along with lighter products. No carbon oxides were detected. In one particular slice of the effluent pulse, flame ionization detector capillary GC indicated about a 6 weight % conversion of propane and a 33% selectivity to 2,3-DMB plus 2-MP. The conversion and selectivity over the entire effluent pulse were not determined, but qualitative mass spectral analysis indicated $C_6$ products throughout the effluent pulse.

The process can be carried out in any of several schemes. In one embodiment, the barium peroxide/oxide oxidizer is circulated in a continuous fashion between an aerobic regeneration zone at 575°–650° C., an anaerobic hydrocarbon reaction zone at temperatures up to 450° C. into which the light alkane is fed, and an anaerobic stripping zone at 575° C. The system can be isobaric at elevated pressure and the reactor can be a riser transfer line as is typically utilized in commercial fluid catalytic cracker deigns. In this process concept, the barium peroxide is in the form of fluidizable particles prepared by well-known techniques such as spray drying.

Since the preferred operating pressure is high, however, other process schemes may be more desirable than fluidized bed reactors. Reactors in which the oxidizer is in the form of packed powder or a monolith may also be utilized with hydrocarbon and air being alternatively fed to each of a bank of reactors in turn.

The invention claimed is:

1. Process for preparing branched-chain paraffins which comprises contacting a $C_3$ or $C_4$ hydrocarbon with a barium peroxide oxidizer in a reaction zone at a temperature of 200°–450° C., sufficient to oxidatively dimerize said hydrocarbon, recovering a branched-chain dimer of said hydrocarbon and barium oxide from the reaction zone, and regenerating said oxidizer by oxidizing said barium oxide to barium peroxide.

2. Process according to claim 1 wherein said hydrocarbon is propane.

3. Process according to claim 1 wherein said hydrocarbon is isobutane.

4. Process according to claim 1 wherein said temperature is 250°–400° C.

5. Process according to claim 1 wherein said regenerating is by heating the barium oxide in the presence of oxygen at a temperature above 400° C.

* * * * *